United States Patent [19]
Badger

[11] Patent Number: 5,708,019
[45] Date of Patent: Jan. 13, 1998

[54] METHODS OF TREATING HYPERLIPIDEMIA USING AZASPIRANE DERIVATIVES

[75] Inventor: Alsion Mary Badger, Bryn Mawr, Pa.

[73] Assignee: SmithKline Beecham Corporation, Philadelphia, Pa.

[21] Appl. No.: 295,777

[22] PCT Filed: Apr. 28, 1994

[86] PCT No.: PCT/US94/04683

§ 371 Date: May 4, 1995

§ 102(e) Date: May 4, 1995

[87] PCT Pub. No.: WO94/25024

PCT Pub. Date: Nov. 10, 1994

[30] Foreign Application Priority Data

Apr. 28, 1993 [GB] United Kingdom ............... 9308780

[51] Int. Cl.$^6$ ............................................. A61K 31/40
[52] U.S. Cl. ............................................. 514/409; 514/824
[58] Field of Search .............................. 514/409, 824

[56] References Cited

U.S. PATENT DOCUMENTS

| 4,291,030 | 9/1981 | Mulinos | 424/245 |
| 4,963,557 | 10/1990 | Badger et al. | 514/278 |

FOREIGN PATENT DOCUMENTS

WO 93/07869  4/1993  WIPO.
WO 93/07871  4/1993  WIPO.

OTHER PUBLICATIONS

Chemical Abstracts, vol. 119, Apr. 1993, Bugelski, et al., abstract No. 80231.
J. Med. Chem. 1990, 33, pp. 2963–2970.

*Primary Examiner*—Kimberly Jordan
*Attorney, Agent, or Firm*—Cushman Darby & Cushman IP Group Pillsbury Madison & Sutro LLP

[57] ABSTRACT

Invented is a method of treatment of hyperlipidemia, in a mammal, including a human, in need thereof which comprises administering to such mammal an effective amount of an azaspirane derivative. Also invented are pharmaceutical compositions containing an azaspirane derivative.

29 Claims, No Drawings

METHODS OF TREATING HYPERLIPIDEMIA USING AZASPIRANE DERIVATIVES

This application is a 371 of PCT/US94/04683, filed Apr. 28, 1994, published as WO94/25024 Nov. 10, 1994.

This invention also relates to pharmaceutical compositions containing an azaspirane derivative.

BACKGROUND OF THE INVENTION

Badger et al., *J. Med. Chem.*, 33, 2963–2970, (1990) describes the structure activity relationships of azaspirane derivatives in antiarthritic and suppressor cell inducing assays. The cited reference disclosed compounds found to be active and inactive in the assays utilized therein. Badger, et al. concluded that one such compound, 2-[2-(dimethylamino)ethyl]-8,8-dipropyl-2-azaspiro[4.5]decane dihydrochloride, exhibited no biologically significant activity.

SUMMARY OF THE INVENTION

This invention relates to a a method of treatment of hyperlipidemia in a mammal, including a human, in need thereof which comprises administering to such mammal an effective amount of a compound of the Formula I

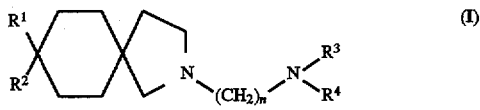

wherein:

n is 1 or 2;

$R^1$ and $R^2$ are the same or different and are selected from hydrogen or straight chain, branched chain or cyclic alkyl, provided that the total number of carbon atoms contained in $R_1$ and $R_2$ when taken together is 0–10; or $R^1$ and $R^2$ are joined together to from a cyclic alkyl group having 3–7 carbon atoms; and $R^3$ and $R^4$ are the same or different and are selected from hydrogen or methyl; or a pharmaceutically acceptable salt, hydrate or solvate thereof.

This invention also relates to pharmacetuical compositions containing compounds of Formula I.

DETAILED DESCRIPTION OF THE INVENTION

The term "hyperlipidemia" as used in the specification and in the claims is meant the presence of an abnormally high level of lipids in the blood.

The term "antihyperlipidemic" as used herein is meant the lowering of excessive lipid concentrations to desired levels.

Preferred lipids, of which high levels thereof are treated by the presently invented methods, are; cholesterol, triglycerides and low-density lipoproteins.

Compounds of Formula (I) can be prepared by known methods such as described in Badger, et al. *J. Med. Chem.*, 33, 2963–2970, (1990) and in U.S. Pat. No. 4,963,557. Pharmaceutically acceptable salts, hydrates and solvates of the compound of structure (I) are formed, when appropriate, by methods well known to those of skill in the art.

Compounds of the present invention which are useful in the treatment of hyperlipidemia and which are included in the pharmaceutical compositions of the invention are those having Formula I

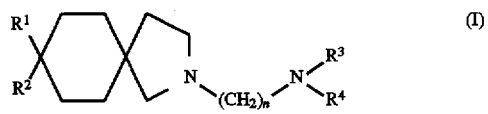

wherein:

n is 1 or 2;

$R^1$ and $R^2$ are the same or different and are selected from hydrogen or straight chain, branched chain or cyclic alkyl, provided that the total number of carbon atoms contained in $R_1$ and $R_2$ when taken together is 0–10; or $R^1$ and $R^2$ are joined together to from a cyclic alkyl group having 3–7 carbon atoms; and $R^3$ and $R^4$ are the same or different and are selected from hydrogen or methyl; or a pharmaceutically acceptable salt, hydrate or solvate thereof.

Preferred among the compounds of Formula I is 2-[2-(dimethylamino)ethyl]-8,8-dipropyl-2-azaspiro[4.5]decane.

As used herein, the term 2-[2-(dimethylamino)ethyl]-8,8-dipropyl-2-azaspiro[4.5]decane refers to a compound of the structure

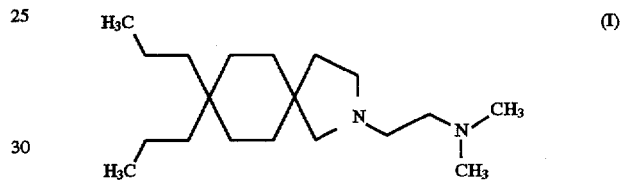

Preferably when the compound 2-[2-(dimethylamino)ethyl]-8,8-dipropyl-2-azaspiro[4.5]decane is utilized as described herein said compound will be in the form of a dihydrochloride salt.

It has now been discovered that compounds of Formula I and pharmaceutically acceptable salts, hydrates and solvates thereof are useful for treatment of hyperlipidemia in a mammal, including humans, in need of such treatment.

2-[2-(dimethylamino)ethyl]-8,8-dipropyl-2-azaspiro[4.5]decane dihydrochloride (hereinafter compound A) was tested for its in vivo potency in lowering serum cholesterol in normal cholesterolemic dogs in two experiments.

To perform experiment I a total of 3 female pure bred normal cholesterolemic beagle dogs (Marshall Animal Farms, Inc., North Rose, N.Y.) were used. The dogs weighed between 8 and 15 kilograms at the start of the study. The dogs were maintained on tap water, which was available ad libitum from an automatic watering system, and standard laboratory chow (Pruina Laboratory Cainine Chow®). The 3 dogs were set up in 3 units and dosed once a day with 1.0 mg/kg of compound A. The cholesterol level of each dog was established on days −21, −14, −7 and day 0 prior to dosing. Dosing began on day 0, after the final pretreatment cholesterol level was taken, and continuted until day 28. The cholesterol levels of each dog was established on days 7, 14, 21 and 28 during treatment. The dogs were fed approximately 300 grams of the canine chow at least 1–2 hours before dosing. The dogs were fasted for approximately 21–23 hours prior to obtaining blood samples.

Experiment II was performed under the same procedure as experiment I. In experiment II 9 female pure bred normal cholesterolemic beagle dogs were set up in 3 groups as follows:

| Group 1 | Control, dosed orally once a day with vehicle alone. |
| Group 2 | Low dose, dosed orally once a day with 1.0 mg/kg of compound A. |
| Group 3 | High dose, dosed orally once a day with 3.0 mg/kg of compound A. |

In Experiment II dosing continued until day 35. The cholesterol level of each dog was established on days 7, 14, 21, 28 and 35 during treatment.

The test compound was administered in a gelatin capsule and control dogs received in an empty capsule. Serum cholesterol levels in the blood samples were determined on an Instramentation Laboratories Monarch chemistry analyzer employing Instramentation Laboratories commercial reagents.

The dogs treated with 2-[2-(dimethylamino)ethyl]-8,8-dipropyl-2-azaspiro[4.5]decane dihydrochloride realized a significant decrease in serum cholesterol levels. Thus, the administration of 2-[2-(dimethylamino)ethyl]-8,8-dipropyl-2-azaspiro[4.5]decane results in a therapeutic lowering of serum cholesterol levels in mammals.

Because the compounds of Formula I lower serum cholesterol they have therapeutic utility in treating hyperlipidemia.

The method of this invention of treating hyperlipidemia comprises administering to a mammal, including humans, in need thereof an effective amount of a compound of Formula I.

An effective antihyperlipidemic amount of a compound of Formula I or a pharmaceutically acceptable salt, hydrate or solvate thereof (i.e. active ingredient) is useful in treating, prophylactically or therapeutically, any disease state in a mammal, including a human, which is exacerbated or caused by excessive lipid levels. Preferably, the disease state is selected from hyperlipidemic syndromes, atherosclerosis and transplant arteriolosclerosis. Particularly preferred is the disease state of atherosclerosis.

This invention relates to a method of treatment of hyperlipidemia in a mammal, including a human, in need thereof which comprises administering an effective amount of a compound of Formula I or a pharmaceutically acceptable salt, hydrate or solvate thereof. This invention also relates to a compound of Formula I or a pharmaceutically acceptable salt, hydrate or solvate thereof in a conventional dosage form prepared by combining a compound of Formula I or a pharmaceutically acceptable salt, hydrate or solvate thereof, with a conventional pharmaceutically acceptable carrier or diluent according to known techniques, such as described in the examples below.

The invention also provides for the use of a compound of the Formula I in the manufacture of a medicament for use in treating hyperlipidemia.

The invention also provides for a pharmaceutical composition for use in the treatment of hyperlipidemia which comprises a compound of Formula I or pharmaceutically acceptable salts, hydrates and solvates and a pharmaceutically acceptable carrier or diluent.

The invention also provides for a process for preparing a pharmaceutical composition containing a pharmaceutically acceptable carrier or diluent and a compound of Formula I or pharmaceutically acceptable salts, hydrates and solvates thereof which comprises bringing said compound into association with the pharmaceutically acceptable carrier or diluent.

No unacceptable toxicological effects are expected when the compositions of the invention are administered in accordance with the present invention.

It will be recognized by one of skill in the art that the form and character of the pharmaceutically acceptable carrier or diluent is dictated by the amount of active ingredient with which it is to be combined, the route of administration and other well-known variables. A compound of Formula I or a pharmaceutically acceptable salt, hydrate or solvate thereof is administered to a mammal, including a human, in need of antihyperlipidemic activity in an amount sufficient to lower lipid concentration to desired levels.

The route of administration of a compound of Formula I is not critical but is usually oral or parenteral, preferably oral. The term parenteral as used herein includes intravenous, intramuscular, subcutaneous, intranasal, intrarectal, transdermal, intravaginal or intraperitoneal administration. The subcutaneous and intramuscular forms of parenteral administration are generally preferred. The daily parenteral dosage regimen will preferably be from about 0.01 mg/kg to about 30 mg/kg of total body weight, most preferably from about 0.1 mg/kg to about 3 mg/kg. The daily oral dosage regimen will preferably be from about 0.01 mg/kg to about 30 mg/kg of total body weight.

Preferably, each parenteral dosage unit will contain the active ingredient in an amount of from about 0.1 mg to about 200 mg. Preferably each oral dosage unit will contain the active ingredient in an amount of from about 1 mg to about 200 mg.

A compound of Formula I can be formulated for example as liquids, for example syrups, suspensions or emulsions, tablets, capsules and lozenges.

A liquid formulation will generally consist of a suspension or solution of a compound of Formula I or pharmaceutically acceptable salt in a suitable liquid carrier(s) for example, ethanol, glycerine, non-aqueous solvent, for example polyethylene glycol, oils, or water with a suspending agent, preservative, flavoring or coloring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

While it is possible for the active ingredient to be administered alone, it is preferable to present it as a pharmaceutical formulation.

It will be recognized by one of skill in the art that the optimal quantity and spacing of individual dosages of a compound of Formula I or a pharmaceutically acceptable salt, hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula I or a pharmaceutically acceptable salt, hydrate or solvate thereof given per day and duration of therapy, can be ascertained by those skilled in the art using conventional course of treatment determination tests.

Following are the results of testing the compounds of this invention.

Table I

The effect of 2-[2-(dimethylamino)ethyl]-8,8-dipropyl-2-azaspiro[4.5]decane dihydrochloride (Compound A) on lowering serum cholesterol levels in normal cholesterolemic dogs from experiment I.

TABLE I

| Unit No. N = 1/unit | Treatment | Cholesterol Level (mg/dl) at Identical days of Treatment | | | | | | | | |
|---|---|---|---|---|---|---|---|---|---|---|
| | | −21 | −14 | −7 | 0 | Pre-treatment mean | 7 | 14 | 21 | 28 |
| Unit 1 | Female 1.0 mg/kg of Compound A | 170 | 149 | 156 | 147 | 156 | 134 | 148 | 123 | 131 |
| Unit 2 | Female 1.0 mg/kg of Compound A | 173 | 184 | 172 | 187 | 179 | 152 | 153 | 143 | 134 |
| Unit 3 | Female 1.0 mg/kg of Compound A | 180 | 201 | 192 | 198 | 193 | 172 | 161 | 124 | 118 |
| | MEAN | 174 | 178 | 173 | 177 | 176 | 153 | 154 | 130 | 128 |
| | SEM | ±3 | ±15 | ±10 | ±15 | ±11 | ±11 | ±4 | ±7 | ±5 |

The data in the above table demonstrates the therapeutic effect of Compound A on serum cholesterol levels.

Table II

The effect of Compound A on lowering serum cholesterol levels in normal cholesterolemic dogs from experiment II.

TABLE II

| Unit No. N = 1/unit | Treatment | Cholesterol level (mg/kg) at identical days of treatment | | | | | | | | | |
|---|---|---|---|---|---|---|---|---|---|---|---|
| | | −21 | −14 | −7 | 0 | Pre-treatment mean | 7 | 14 | 21 | 28 | 35 |
| Unit 1 | None Female Control | 153 | 159 | 156 | 170 | 160 | 155 | 153 | 153 | 155 | 148 |
| Unit 2 | None Female Control | 179 | 179 | 164 | 163 | 171 | 148 | 147 | 141 | 149 | 155 |
| Unit 3 | None Female Control | 214 | 197 | 214 | 200 | 206 | 182 | 179 | 190 | 191 | 178 |
| | Control MEAN | 182 | 178 | 178 | 178 | 179 | 162 | 160 | 161 | 165 | 160 |
| | Control SEM | 118 | 111 | 118 | 111 | 114 | 110 | 110 | 115 | 113 | 49 |
| Unit 4 | Female 1.0 mg/kg of compound A | 148 | 164 | 173 | 216 | 175 | 171 | 169 | 163 | 150 | 148 |
| Unit 5 | Female 1.0 mg/kg of compound A | 167 | 158 | 146 | 153 | 156 | 124 | 124 | 110 | 101 | 103 |
| Unit 6 | Female 1.0 mg/kg of compound A | 210 | 251 | 266 | 270 | 249 | 226 | 185 | 190 | 181 | 179 |
| | 1.0 mg/kg MEAN | 175 | 191 | 195 | 213 | 194 | 174 | 159 | 154 | 144 | 143 |
| | 1.0 mg/kg SEM | ±18 | ±30 | ±36 | ±34 | ±28 | ±29 | ±18 | ±23 | ±23 | ±22 |
| Unit 7 | Female 3.0 mg/kg of compound A | 142 | 143 | 137 | 148 | 143 | 112 | 118 | 106 | 93 | 86 |
| Unit 8 | Female 3.0 mg/kg of compound A | 171 | 167 | 163 | 179 | 170 | 131 | 107 | 90 | 88 | 107 |
| Unit 9 | Female 3.0 mg/kg of compound A | 262 | 289 | 286 | 274 | 278 | 188 | 160 | 138 | 139 | 139 |
| | 3.0 mg/kg MEAN | 192 | 200 | 195 | 200 | 197 | 144 | 128 | 111 | 107 | 411 |
| | 3.0 mg/kg SEM | ±36 | ±45 | ±46 | ±38 | ±41 | ±23 | ±16 | ±14 | ±16 | ±15 |

The data in the above table demonstrates the therapeutic effect of Compound A on serum cholesterol levels.

In addition, the compound of Formula I can be co-administered with further active ingredients, such as other compounds known for the treatment of elevated lipid levels such as acyl-CoA: Cholesterol acyltransferase (ACAT) inhibitors, HMGCoA reductase inhibitors and bile acid sequestrants.

Without further elaboration, it is believed that one skilled in the art can, using the preceding description, utilize the present invention to its fullest extent. The following examples are, therefore, to be construed as merely illustrative and not a limitation of the scope of the present invention in any way.

EXAMPLE 1

Capsule Composition

An oral dosage form for administering Compound A is produced by filing a standard two piece hard gelatin capsule with the ingredients in the proportions shown in Table III, below.

TABLE III

| INGREDIENTS | AMOUNTS |
| --- | --- |
| 2-[2-(dimethylamino)ethyl]-8,8-dipropyl-2-azaspiro[4.5]decane dihydrochloride | 25 mg |
| Lactose | 55 mg |
| Talc | 16 mg |
| Magnesium Stearate | 4 mg |

EXAMPLE 2

Injectable Parenteral Composition

An injectable form for administering Compound A is produced by stirring 1.5% by weight of 2-[2-(dimethylamino)ethyl]-8,8-dipropyl-2-azaspiro[4.5]decane dihydrochloride in 10% by volume propylene glycol in water.

EXAMPLE 3

Tablet Composition

The sucrose, calcium sulfate dihydrate and Compound A shown in Table IV below, are mixed and granulated in the proportions shown With a 10% gelatin solution. The wet granules are screened, dried, mixed with the starch, talc and stearic acid, screened and compressed into a tablet.

TABLE IV

| Ingredients | Amounts |
| --- | --- |
| 2-[2-(dimethylamino)ethyl]-8,8-dipropyl-2-azaspiro[4.5]decane dihydrochloride | 20 mg |
| calcium sulfate dihydrate | 30 mg |
| sucrose | 4 mg |
| starch | 2 mg |
| talc | 1 mg |
| stearic acid | 0.5 mg |

While the above descriptions and examples fully describe the invention and the preferred embodiments thereof, it is understood that the invention is not limited to the particular disclosed embodiments coming within the scope of the following claims.

What is claimed is:

1. A method of treatment of hyperlipidemia in a mammal in need thereof which comprises administering to such mammal an effective amount of a compound of Formula I

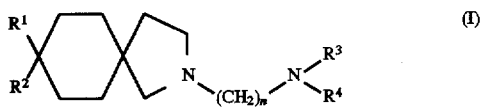

wherein:

n is 1 or 2;

$R^1$ and $R^2$ are the same or different and are selected from hydrogen or straight chain, branched chain or cyclic alkyl, provided that the total number of carbon atoms contained in $R_1$ and $R_2$ when taken together is 0–10; or $R^1$ and $R^2$ are joined together to from a cyclic alkyl group having 3–7 carbon atoms; and $R^3$ and $R^4$ are the same or different and are selected from hydrogen or methyl; or a pharmaceutically acceptable salt, hydrate or solvate thereof.

2. The method of claim 1 wherein the compound is 2-[2-(dimethylamino)ethyl]-8,8-dipropyl-2-azaspiro[4.5]decane.

3. The method of claim 1 wherein the mammal is a human.

4. The method of claim 1 wherein the mammal is afflicted with hyperlipidemic syndrome.

5. The method of claim 1 wherein the mammal is afflicted with atherosclerosis.

6. The method of claim 1 wherein the mammal is afflicted with transplant arteriolosclerosis.

7. The method of claim 1 wherein the mammal is in need of lower cholesterol and triglyceride levels.

8. The method of claim 1 wherein the mammal is in need of lower cholesterol levels.

9. The method of claim 1 wherein the mammal is in need of lower triglyceride levels.

10. The method of claim 1 wherein the mammal is in need of lower low-density lipoprotein levels.

11. The method of claim 1 wherein the compound is administered orally.

12. The method of claim 11 wherein from about 0.01 mg/kg to about 30 mg/kg of compound is administered per day.

13. The method of claim 1 wherein the compound is administered parenteraly.

14. The method of claim 13 wherein from about 0.01 mg/kg to about 30 mg/kg of compound is administered per day.

15. A pharmaceutical composition comprising a compound of the structure:

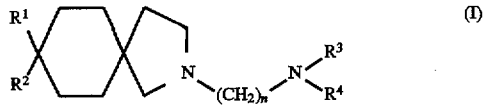

wherein:

n is 1 or 2;

$R^1$ and $R^2$ are the same or different and are selected from hydrogen or straight chain, branched chain or cyclic alkyl, provided that the total number of carbon atoms contained in $R_1$ and $R_2$ when taken together is 0–10; or $R^1$ and $R^2$ are joined together to from a cyclic alkyl group having 3–7 carbon atoms; and $R^3$ and $R^4$ are the same or different and are selected from hydrogen or methyl; or a pharmaceutically acceptable salt, hydrate or solvate thereof; and a pharmaceutically acceptable carrier.

16. A composition according to claim 15 wherein the compound is 2-[2-(dimethylamino)ethyl]-8,8 -dipropyl-2-azaspiro[4.5]decane.

17. A composition according to claim 15 wherein the mammal being treated is a human.

18. A composition according to claim 15 wherein the mammal is afflicted with hyperlipidemic syndrome.

19. A composition according to claim 15 wherein the mammal is afflicted with atherosclerosis.

20. A composition according to claim 15 wherein the mammal is afflicted with transplant arteriolosclerosis.

21. A composition according to claim 15 wherein the mammal is in need of lower cholesterol and triglyceride levels.

22. A composition according to claim 15 wherein the mammal is in need of lower cholesterol levels.

23. A composition according to claim 15 wherein the mammal is in need of lower triglyceride levels.

24. A composition according to claim 15 wherein the mammal is in need of lower low-density lipoprotein levels.

25. A composition according to claim 15 wherein the compound is administered orally.

26. A composition according to claim 25 wherein from about 0.01 mg/kg to about 30 mg/kg of compound is administered per day.

27. A composition according to claim 15 wherein the compound is administered parenterally.

28. A composition according to claim 27 wherein from about 0.01 mg/kg to about 30 mg/kg of compound is administered per day.

29. A pharmaceutical composition comprising a pharmaceutically acceptable carrier and a compound of the structure

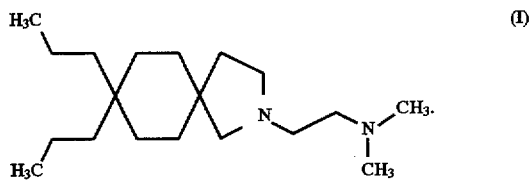

(I)

* * * * *